US009420975B2

(12) United States Patent
Gutfleisch et al.

(10) Patent No.: US 9,420,975 B2
(45) Date of Patent: Aug. 23, 2016

(54) IMAGING FACILITY AND RADIATION THERAPY DEVICE

(75) Inventors: Marcus Gutfleisch, Erlangen (DE); Thomas Knöfel, Pressath (DE); Gerhard Lechsel, Erlangen (DE); Alexander Passin, Forchheim (DE); Thomas Tücking, Röttenbach (DE)

(73) Assignee: Siemens Aktiengesellschaft, München (DE)

( * ) Notice: Subject to any disclaimer, the term of this patent is extended or adjusted under 35 U.S.C. 154(b) by 51 days.

(21) Appl. No.: 13/178,949

(22) Filed: Jul. 8, 2011

(65) Prior Publication Data

US 2012/0177171 A1    Jul. 12, 2012

(30) Foreign Application Priority Data

Jul. 9, 2010  (DE) .................. 10 2010 026 674

(51) Int. Cl.
*G01N 23/04* (2006.01)
*A61N 5/10* (2006.01)
*A61B 6/03* (2006.01)
*A61B 6/02* (2006.01)
*A61B 6/00* (2006.01)

(52) U.S. Cl.
CPC ............. *A61B 6/032* (2013.01); *A61B 6/025* (2013.01); *A61B 6/4085* (2013.01); *A61B 6/4452* (2013.01); *H05K 999/00* (2013.01)

(58) Field of Classification Search
CPC ....... A61B 6/4452; A61B 6/025; A61B 6/032
USPC .................... 378/11, 19, 4, 62, 146
See application file for complete search history.

(56) References Cited

U.S. PATENT DOCUMENTS

| 4,903,204 | A | * | 2/1990 | Dobbins, III | ......... G06T 11/006 378/4 |
| 5,410,584 | A | | 4/1995 | Schaefer et al. | |
| 6,256,370 | B1 | * | 7/2001 | Yavuz | .............. 378/22 |
| 6,435,714 | B1 | * | 8/2002 | Bruder | .......... 378/196 |
| 6,842,502 | B2 | | 1/2005 | Jaffray et al. | |
| 6,956,925 | B1 | * | 10/2005 | Hoffman | .......... 378/4 |

(Continued)

FOREIGN PATENT DOCUMENTS

| CN | 1643371 A | 7/2005 |
| CN | 1671324 A | 9/2005 |

(Continued)

OTHER PUBLICATIONS

German Office Action dated Jun. 9, 2011 for corresponding German Patent Application No. DE 10 2010 026 674.4 with English translation.

(Continued)

*Primary Examiner* — David J Makiya
*Assistant Examiner* — Dani Fox
(74) *Attorney, Agent, or Firm* — Lempia Summerfield Katz LLC

(57) ABSTRACT

An imaging facility having an X-ray source, an X-ray detector, and a rotation facility operable to rotate the X-ray source and the X-ray detector around a center of rotation. The imaging facility also has a first translation facility operable to move the X-ray source in a direction that has a component that is tangential to a circle of rotation around the center of rotation.

22 Claims, 4 Drawing Sheets

(56) References Cited

U.S. PATENT DOCUMENTS

| | | | |
|---|---|---|---|
| 6,980,624 B2 * | 12/2005 | Li | A61B 6/025 378/22 |
| 7,110,487 B2 * | 9/2006 | Baba et al. | 378/11 |
| 7,409,033 B2 * | 8/2008 | Zhu et al. | 378/4 |
| 7,505,554 B2 | 3/2009 | Ting | |
| 7,519,151 B1 | 4/2009 | Shukla et al. | |
| 2003/0007601 A1 | 1/2003 | Jaffray et al. | |
| 2003/0076927 A1 | 4/2003 | Nakashima et al. | |
| 2003/0194050 A1 * | 10/2003 | Eberhard et al. | 378/37 |
| 2004/0258195 A1 | 12/2004 | Hara | |
| 2006/0023830 A1 | 2/2006 | Schomberg | |
| 2007/0086566 A1 * | 4/2007 | Gregerson et al. | 378/19 |
| 2009/0080603 A1 * | 3/2009 | Shukla et al. | 378/25 |
| 2010/0232565 A1 | 9/2010 | Ye et al. | |
| 2011/0301449 A1 * | 12/2011 | Maurer, Jr. | 600/411 |
| 2014/0205074 A1 | 7/2014 | Gregerson et al. | |
| 2014/0247919 A1 | 9/2014 | Zhang et al. | |

FOREIGN PATENT DOCUMENTS

| | | |
|---|---|---|
| CN | 101466313 A | 6/2009 |
| CN | 101505658 A | 8/2009 |
| DE | 10 2005 004 502 A1 | 8/2006 |
| DE | 10 2005 014 188 A1 | 10/2006 |

OTHER PUBLICATIONS

Chinese Office Action dated Jun. 30, 2014 for corresponding Chinese Patent Application No. 201110264914.5 with English translation.

* cited by examiner

IMAGING FACILITY AND RADIATION THERAPY DEVICE

This application claims the benefit of DE 10 2010 026 674.4, filed Jul. 9, 2010.

BACKGROUND

The present embodiments relate to an imaging facility with an X-ray source and an X-ray detector and are used to produce medical images. The present embodiments further relate to a radiation therapy device with the imaging facility.

Radiation therapy is an established way to treat tumors. During this procedure, a therapeutic treatment beam, such as, for example, an X-ray beam of high-energy X-rays in the MV range, is directed onto a patient to be irradiated. To ensure that the treatment beam precisely irradiates the tissue that forms the tumor, the patient is positioned accurately relative to the treatment beam.

Known radiation therapy devices have an imaging facility in addition to the therapeutic radiation source. Known devices may thus produce medical images with diagnostic X-rays. The diagnostic X-rays are often referred to as kV X-rays, which are different than therapeutic MV X-rays. Devices of this type allow the position of the patient to be monitored before and/or during a treatment.

U.S. Pat. No. 6,842,502 discloses a radiation therapy device with an imaging facility that may be used for cone-beam Computed Tomography (CT). This imaging facility allows three-dimensional datasets of a patient to be recorded.

SUMMARY AND DESCRIPTION

More flexible use of radiation therapy with accurate possible images of the patient may be generated. Such further development is, however, not restricted to imaging facilities for radiation therapy devices, but can be generally employed for imaging facilities.

The present embodiments may obviate one or more of the drawbacks or limitations in the related art. For example, an imaging facility and a radiation therapy device that allows precise imaging and may be used in a flexible manner may be provided.

In the present embodiments, an imaging facility includes an X-ray source and an X-ray detector. The imaging facility further includes a rotation facility operable to rotate the X-ray source and the X-ray detector around a center of rotation, and a translation facility operable to move the X-ray source in a direction that has a component that runs tangentially or is tangential to a circle of rotation around the center of rotation.

The X-ray source may be moved to different positions using the translation facility. The different positions may, for example, be reached by a linear translation of the X-ray source. Accordingly, X-rays may be directed onto the X-ray detector from any of these different positions, such that different beam geometries may be generated. Using these different beam geometries, different imaging modalities may, for example, be carried out.

To switch between the different imaging positions, the X-ray source may be moved in a purely linear manner using, for example, the translation facility. The translation facility may have a rail construction. Using the translation facility, the entire X-ray source may be moved (i.e., the X-ray emitter is moved as a complete constructional unit). In turn, the location of the beam spot from which the X-rays are generated moves as well.

The translation facility may also move the X-ray source in a direction which is tangential to the circle of rotation. Starting from a first imaging position, it is thus possible to align the beam cone emitted from the X-ray source centrally on the center of rotation. In a further imaging position, it is possible to align the beam cone eccentrically on the center of rotation, such that the beam cone runs past the center of rotation.

The middle beam of the beam cone emitted by the X-ray source may strike the X-ray detector at a perpendicular angle, even when the X-ray source is in different positions. However, the beam emitted by the X-ray source that passes through the center of rotation hits the X-ray detector at a different angle depending on the position of the X-ray source. In one position, the beam that runs through the center of rotation may strike the detector at a perpendicular angle. In other positions, however, the beam strikes the detector at an angle that does not equal 90°.

In some embodiments, the imaging facility may also have a second translation facility for moving the X-ray detector. The second translation facility moves the X-ray detector in a direction that has a component that is tangential to a circle of rotation of the X-ray detector around the center of rotation.

In one embodiment, the X-ray detector may be moved in a similar manner as the X-ray source. The position of the X-ray detector may thus be adapted according to the position of the X-ray source in order to, for example, optimize the beam geometry. In turn, it is then possible to employ a smaller X-ray detector. The detector surface struck by the beam may be adapted and/or tuned to the position of the beam path emitted by the X-ray source.

In one embodiment, the translation facility for the X-ray source and the translation facility for the X-ray detector may be arranged such that the X-ray detector may be moved parallel to or in parallel with the X-ray source. For example, the X-ray detector may be moved in a direction that is parallel to the direction in which the X-ray source is moved.

The imaging facility may be operated in a first operating mode in which image data is recorded while the X-ray source and the X-ray detector are rotated around the center of rotation. In the first operating mode, the X-ray source and the X-ray detector are aligned relative to each other such that the central beam of the X-ray source essentially runs through the center of rotation. The imaging facility may also be operated in a second operating mode in which image data is recorded while the X-ray source and the X-ray detector are rotated around the center of rotation. In the second operating mode, the X-ray source is moved, compared to its position in the first operating mode, using the translation facility, such that the central beam emitted by the X-ray source runs laterally past the center of rotation.

In the first operating mode, the central ray of the X-ray cone essentially runs through the center of rotation of the imaging facility. This operating mode allows a three-dimensional image of an object under examination to be reconstructed to map a certain field of view (FOV).

By comparison, the second operating mode allows a three-dimensional image to be reconstructed to map an extended field of view ("extended FOV"). The reconstruction of an enlarged image volume is thus made possible.

An extended FOV may also be obtained by rotating, instead of moving, the cone beam emitted by the X-ray source to an eccentric position past the center of rotation. By permitting movement of the X-ray source, the X-ray detector may be moved more gradually or may have a smaller spread (if the changed beam geometry is compensated for instead of the size of the detector) than known X-ray detectors and yet still achieve a comparable expanded FOV.

In addition, because the X-ray detector is in a less eccentric position during the extended FOV mode, the X-ray detector has a smaller lever arm. As a result, the entire system is subject to fewer mechanical vibrations, resulting in fewer adverse effects on image quality.

In one embodiment, the imaging facility may have a processor unit that reconstructs a three-dimensional image from the image data recorded during the rotation. The processor unit may be operable to weight the recorded image data during the reconstruction. During reconstruction, the weight of an image from image data recorded in the first operating mode has a different weight than the weight of an image from image data recorded in the second operating mode. Since the weighting takes account of the recorded raw image data of the changed beam geometry, the image quality may be improved. In one embodiment, the imaging facility may be operated in a tomosynthesis mode in which the X-ray source is activated at different translation positions to generate a plurality of image datasets. Using the plurality of generated image datasets, a tomosynthesis image may be reconstructed. While the X-ray source is moved to different imaging positions, the imaging facility may be held at a fixed angle of rotation. The X-ray detector may be moved antagonistically in a corresponding manner. For example, if the X-ray source moves to the left, the X-ray detector moves to the right, and vice-versa. In addition to the translational movement of the X-ray source, the X-ray cone emitted by the X-ray source may be pivoted so that the X-ray cone strikes the detector. In one embodiment, the reconstruction of the tomosynthesis image may be controlled by a processor unit that processes the recorded image data for this purpose.

Compared to known examples in which a tomography or tomosynthesis is merged using a number of sources statically arranged alongside one another or in which a fixed source-detector arrangement with a gantry is rotated around the patient, the present embodiments may offer a less complex and time-consuming reconstruction and/or image data recordation process.

A position of the X-ray source may be set by controlling the translation facility to compensate for positioning errors arising from deflections of holders on the imaging facility.

The position of the X-ray source may also be adjusted automatically using, for example, a control facility. In one embodiment, the position of the X-ray source may be dynamically adapted while the imaging facility is rotated around the center of rotation. The adaptation compensates for the positioning errors which vary during the rotation as various components, such as a mechanical holder, bend or are bent. The device may directly compensate for the positioning errors. Advantageously, the source is thus typically located in an error-free ideal position, unlike known systems that compensate for mechanical bending using corresponding recording software with associated calibration. Complex calibrations are thus avoided.

In one embodiment, the radiation therapy device includes a therapeutic radiation source and an inventive imaging facility. The therapeutic radiation source produces a therapeutic treatment beam that may be directed onto an object to be irradiated.

In another embodiment, the radiation therapy device may include a gantry, configured to be rotated around an isocenter, to accommodate the therapeutic radiation source. The gantry may have an overhanging arm from which the therapeutic X-rays are directed onto the isocenter.

The imaging facility may be attached to the gantry. In this way, rotation of the gantry may cause or result in the rotation of the imaging facility around the center of rotation. The center of rotation of the imaging facility may thus coincide with the isocenter of the radiation therapy device.

The imaging facility may be arranged in the radiation therapy device such that the translation facility may move the X-ray source between at least two imaging positions. In such a situation, the X-ray source is, in one of the imaging positions, is positioned opposite the therapeutic radiation source or lies in the axis of the isocentric central beam of the therapeutic radiation.

Accordingly, a few imaging positions may be arranged such that the passage of the emitted X-rays is precisely opposite the therapeutic treatment beam. This is especially advantageous when the patient is being positioned. The translation facility may move the X-ray source in a direction that lies parallel to or in the plane of rotation of the gantry and is perpendicular to the central axis of the therapeutic treatment beam.

In some embodiments, the radiation therapy device may include an X-ray source holder that is configured to allow the X-ray source to be moved from a parked position into an imaging position.

The holder thus allows the X-ray source to be moved to a parked position in which the X-ray source is no longer struck by the therapeutic X-rays. The holder may, for example, move the X-ray source into a parked position by performing a linear movement that is perpendicular to the plane of rotation of the gantry. In contrast, the translation facility may carry out a translational movement that is perpendicular to this direction. In one embodiment, the translation facility may be integrated into the holder.

DETAILED DESCRIPTION OF THE DRAWINGS

Figure 1:
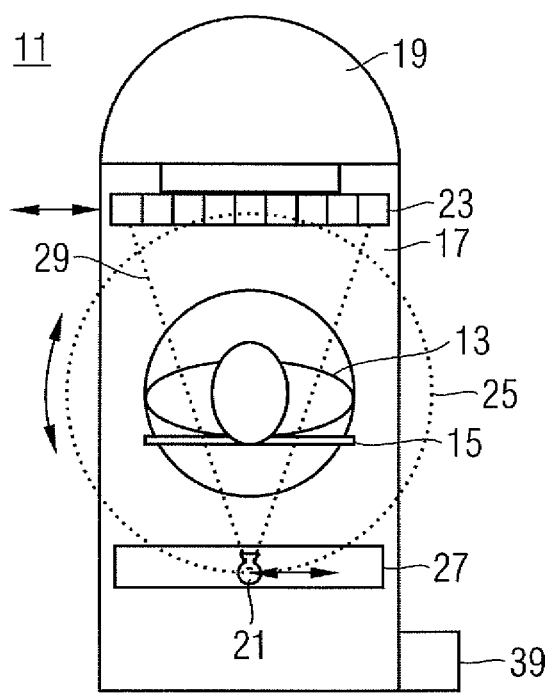
FIG. 1 shows a front view of one embodiment of a radiation therapy device having a kV source arranged opposite a therapeutic MV source.

FIG. 1 shows a front view of a radiation therapy device 11. A patient 13 may be centrally placed or located on a patient bed 15. A gantry 17, bearing components of the radiation therapy device 11, may be rotated around the patient 13. The gantry 17 is shown in the upright position in FIG. 1.

In this position, the gantry 17 has an overhanging arm 19 at the top in which components of the accelerator and the beam-forming elements are arranged. The therapeutic radiation is initially focused in the overhanging arm 19. The therapeutic radiation may be directed onto the patient 13 from the overhanging arm 19. For the sake of clarity, the beam path of the therapeutic radiation is not shown in FIG. 1.

The radiation therapy device 11 features an imaging facility. The imaging facility includes an X-ray source 21 for diagnostic X-rays. The X-ray source 21 is arranged on the other side of the patient 13 opposite the overhanging arm 19. Diagnostic X-rays are directed from the X-ray source 21, in a direction opposite to the direction of the therapeutic radiation, onto an X-ray detector 23. With the aid of this imaging facility, fluoroscopy images of the patient may be produced.

The imaging facility may be operated in a so-called cone-beam mode. In this mode, the gantry 17 is rotated around the patient 13 and projection images of the patient 13 are produced from a plurality of different angles. A three-dimensional cone beam computed tomography may be reconstructed from the projection images.

When the gantry 17 is rotated, the X-ray source 21 is moved around a virtual circle of rotation 25. The radiation therapy device 11 also includes a translation facility 27 that operates to move or displace the X-ray source 21 in a linear manner. In one embodiment, the X-ray source 21 is displaced in a direction that is tangential to the circle of rotation 25.

The X-ray detector 23 may likewise be moved. As with the X-ray source 21, the X-ray detector 23 may be linearly moved or displaced in a direction that is tangential to the virtual circle of rotation 25. The X-ray source 21 and the X-ray detector 23 may, for example, be moved by the same amount in parallel to one another.

Figure 2:
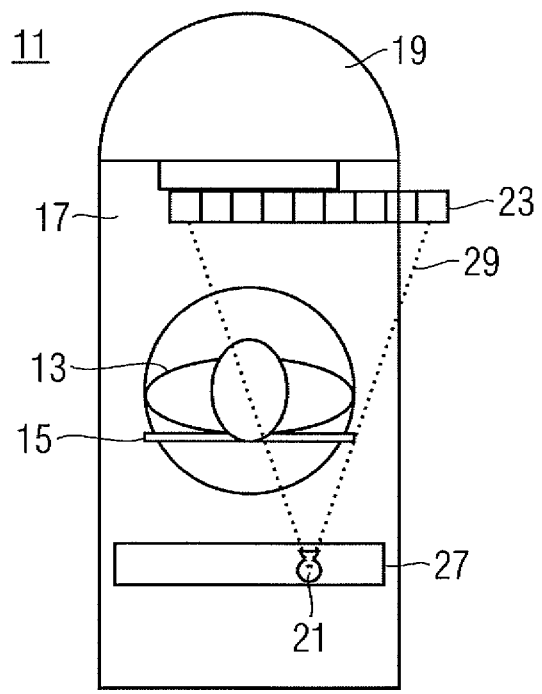
FIG. 2 shows a front view of one embodiment of a radiation therapy device having a slightly displaced X-ray source and X-ray detector.

With reference to FIG. 2, the cone beam 29 emitted by the X-ray source 21 is moved parallel to the main axis of the therapeutic beam path. When the gantry 17 is rotated and projection images are produced with the imaging facility, a cone beam computed tomography with an extended field of view may be produced. As a result, better images of larger patients or larger tumors may be produced.

The linear movement of the X-ray source 21 and of the X-ray detector 23 may also be used, with, for example, the same angular position of the gantry, to produce a tomosynthesis image. For this purpose, the X-ray source and the X-ray detector are activated during a translational movement.

Figure 3:
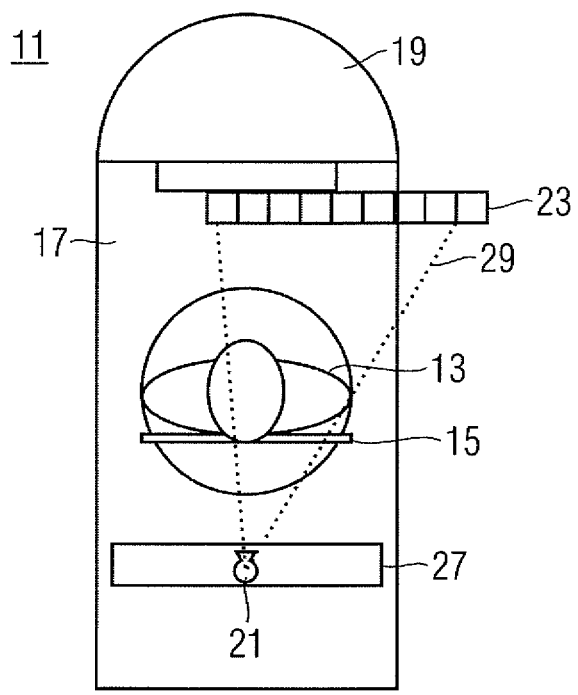
FIG. 3 shows a front view of one embodiment of a radiation therapy device having a slightly rotated X-ray beam path and a displaced X-ray detector.

In contrast, the embodiment depicted in FIG. 3 obtains an extended field of view in a different way. In this embodiment, only the X-ray detector 23 is moved and the cone beam 29 emitted by the X-ray source 21 is rotated so that it strikes the moved detector 23. Because the X-ray source 21 may be rotated but not otherwise moved a tomosynthesis image may not be produced.

Figure 4:
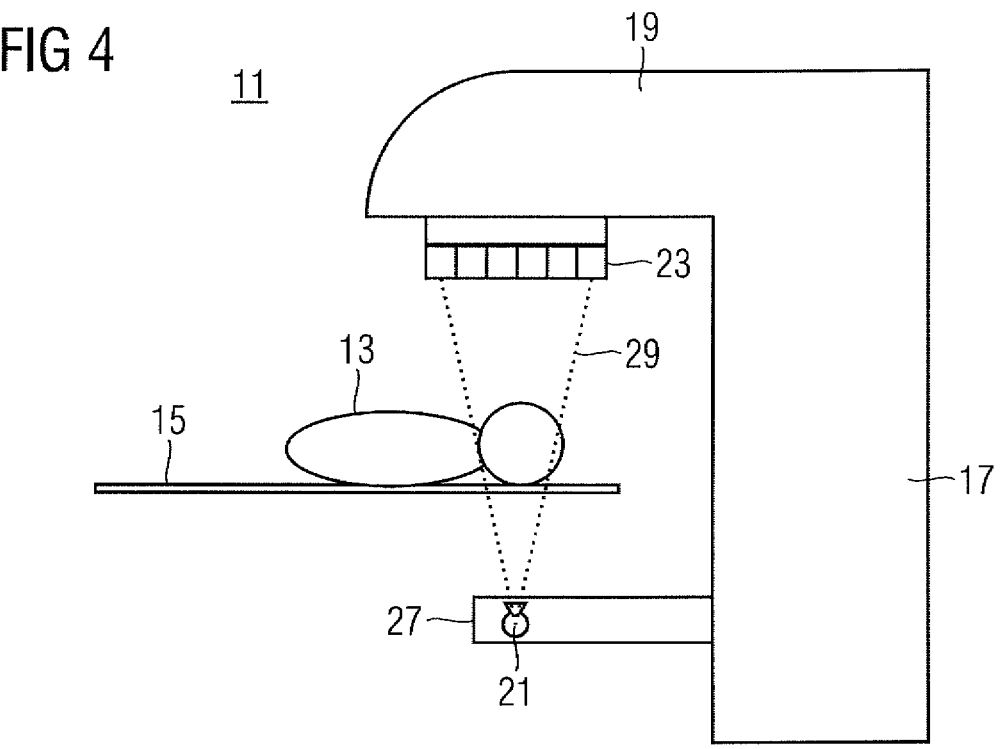
FIG. 4 shows a side view of one embodiment of a radiation therapy device.

FIG. 4 shows a side view of the radiation therapy device 11 shown in FIGS. 1 and 2.

In FIG. 4, the gantry 17 with the overhanging arm 19 is visible. The X-ray source 21 and the X-ray detector 23 are located in an imaging position. In other words, the X-ray source 21 and the X-ray detector 23 have been suitably moved from a withdrawn parked position such that the X-ray source 21 may X-ray an already properly positioned patient 13.

Figure 5:
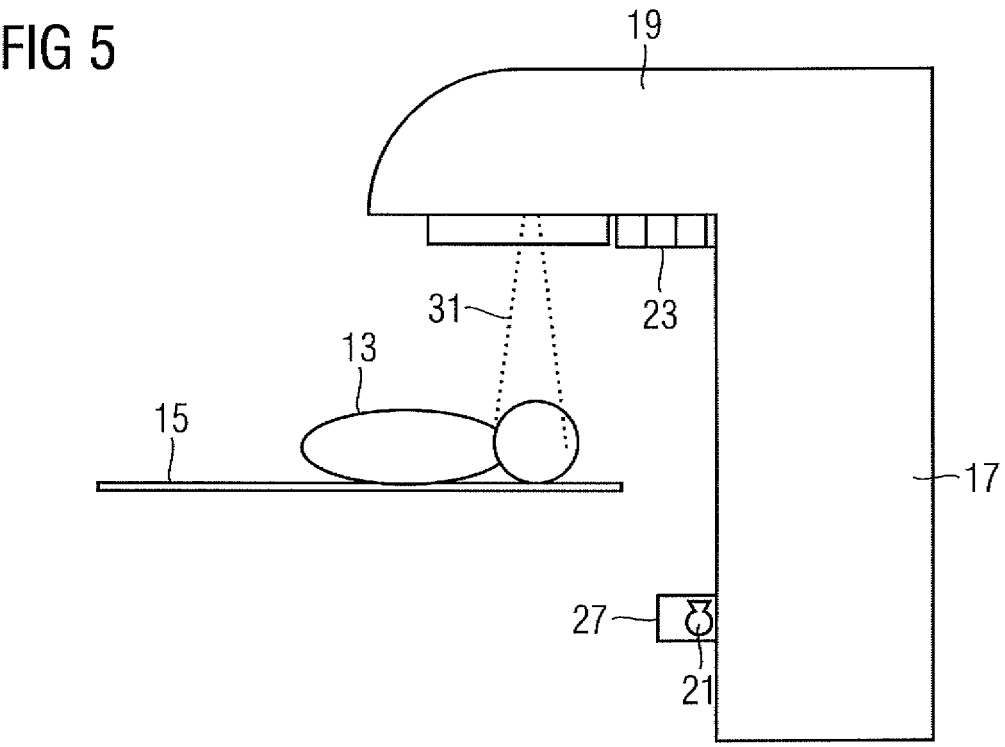
FIG. 5 shows a side view of one embodiment of a radiation therapy device having a retracted X-ray source and a retracted X-ray detector.

In contrast, in FIG. 5, the X-ray source 21 and the X-ray detector 23 are located in the withdrawn parked position. The withdrawn parked position may be assumed when the therapeutic beam 31 is directed onto the patient 13 in order to remove the imaging facility from the therapeutic beam 31.

FIG. 4 illustrates the projection of both the radiation therapy device depicted in FIG. 1, in which the X-ray source 21 and of the X-ray detector 23 are centrally and concentrically arranged, and the radiation therapy device 11 depicted in FIG. 2, in which the X-ray source 21 and the X-ray detector 23 are eccentrically arranged.

Figure 6:
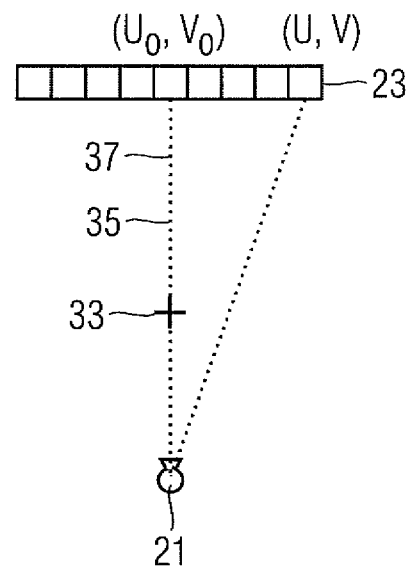
FIG. 6 and FIG. 7 show a diagram of the beam paths for a centered or eccentric imaging facility.

FIG. 6 shows the coordinates used when the X-ray source 21 is centrally arranged. The X-ray source 21 and X-ray detector 23 are thus positioned opposite one another such that the concentric central X-ray beam 35 passes through the center of rotation 33 and is, simultaneously, the isocentric beam 37.

Figure 7:
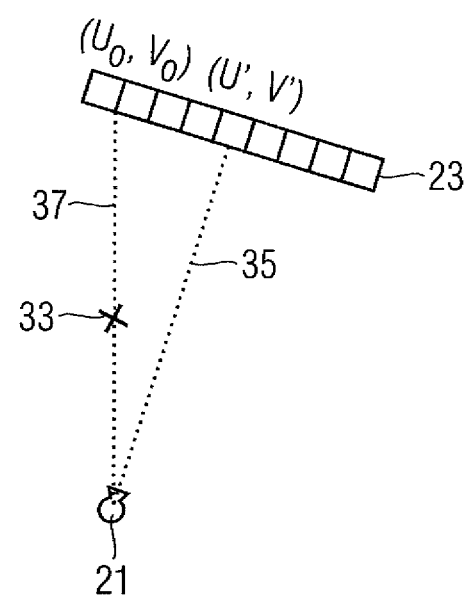

FIG. 7, on the other hand, illustrates an embodiment in which the X-ray source 21 and the X-ray detector 23 are moved in parallel with one another. The emitted concentric X-ray beam thus no longer passes through the center of rotation 33. Expressed differently, the isocentric beam 37 that passes through the center of rotation 33 no longer strikes the center of the X-ray detector 23.

Aspects of the reconstruction, as well as a weighting that is performed before the actual reconstruction, will now be described.

To enlarge the field of view, the flat panel detector is offset relative to a centered arrangement. Since the beam angle of the X-ray source is limited, the X-ray source is moved in a parallel with the flat panel detector so that the beam passage may cover an enlarged field of view.

A three-dimensional image may be obtained, using, for example, filtered back projection methods, if parallel beam projections from 180° are available. For an expanded field of view, parallel beam projections occur when the cone beam 29 covers half the field of view. As a result, the isocenter or center of rotation 33 may be covered by the cone beam 29.

In contrast to conventional cone beam imaging, the isocentric beam 37, which is the beam that passes through the isocenter 33 from the X-ray source 21, no longer strikes the flat panel detector 23 at a perpendicular angle.

The recorded raw image data may be weighted. The weighting process may, for example, be carried out by a processor unit that processes the recorded image data and reconstructs, for example, a cone beam CT.

If an image reconstruction takes place with a centered X-ray source, a pre-weighting of the image data may be carried out using the following formula:

$$\text{Pre-weight}(u, v, \beta) = \frac{D}{\sqrt{f^2 + x_r^2 + y_r^2}}$$

$$= \frac{f/p_x}{\sqrt{(f/p_x)^2 + (x_r/p_x)^2 + (y_r/p_x)^2}} \cdot \frac{D}{f}$$

where f refers to the SID ("source imager distance"), D refers to the SAD ("source-to-axis distance"), β refers to the angle of rotation of the emitted cone beam, (u, v) refers to the coordinates of the pixel, and $x_r$ or $y_r$ refer to the coordinates of the pixel relative to the point of contact $(u_0, v_0)$ of the isocentric beam 37.

If the X-ray source is moved, the pre-weighting may be changed. Instead of a weighting related to the isocentric beam 37, the pixels are weighted, which is done in relation to a beam 35 that strikes the flat panel detector 23 at a perpendicular angle.

The following process may thus be utilized: (1) adapting or adjusting the projection matrix used for the calculation to reflect the translation of the flat panel detector, (2) determining the beam that strikes the flat panel detector at a perpendicular angle (point of impact (u',v')), and (3) performing the pre-weighting using the coordinates $(x_r, y_r)$ related to (u',v').

The flat panel detector and the X-ray source may shift to a different degree. The above-described algorithm is applicable when the flat panel detector and the X-ray source shift in parallel with one another.

If the source is shifted, for example, by the amount d, the new point (u',v') may be determined using the projection matrix. The projection matrices for an X-ray source in the center $P^\beta$ and a shifted X-ray source $Q^\beta$ are compared to one another. $P^\beta$ and $Q^\beta$ differ in a translational parameter. All other coefficients do not change. The position of the projected isocenter changes in accordance with the following: −SID/SAD·d. Consequently, the following is produced:

$$q_{03} = p_{03} + \text{SID/SAD} \cdot d \qquad 5$$

The projection matrix $Q^\beta$ may, for example, be determined during a geometric calibration for the expanded field of view with a shifted X-ray source. The point $(u_0, v_0)$ is always identical to the coefficients $(p_{03}, p_{13})$, or, in other words, is always identical to the projected isocenter of the projection matrix (imaging of the coordinates $(0,0,0)$). Thus, the following applies:

$$(u', v') = (q_{03} - \text{SID/SAD} \cdot d, q_{13}).$$

This equation is independent of the projection angle $\beta$.

To make individual projections from which a reconstruction is undertaken, around 400 projection images may, for example, be recorded from different projection directions.

It is advantageous to keep the translation of the X-ray source as small as possible, especially when a high quality image is desired. By doing so, the mechanical accuracy is increased and the influence of the weighting factors on, for example, the isocentric beam is reduced.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An imaging facility comprising:
   an X-ray source operable to emit a cone beam;
   an X-ray detector, wherein the X-ray source, the X-ray detector, or the X-ray source and the X-ray detector are positionable such that an isocentric beam emitted by the X-ray source strikes a surface of the X-ray detector at different angles relative to the surface;
   a rotation facility operable to rotate the X-ray source and the X-ray detector around a center of rotation;
   a first translation facility configured to move the X-ray source from a first position relative to a portion of the rotation facility in a direction that has a component that is tangential to a circle of rotation around the center of rotation;
   a second translation facility configured to move the X-ray detector from a second position relative to the portion of the rotation facility, wherein the imaging facility is operable in a first operating mode and a second operating mode, wherein in the first operating mode, image data is recorded while the X-ray source and the X-ray detector are aligned with each other such that a central beam of the X-ray source essentially passes through the center of rotation, and wherein in the second operating mode, image data is recorded when the X-ray source and the X-ray detector are moved by the first translation facility and the second translation facility, respectively, to be aligned with each other such that the central beam emitted by the X-ray source runs laterally past the center of rotation; and
   a processor unit configured to reconstruct a three-dimensional image from the image data recorded while the X-ray source and the X-ray detector are rotated, wherein the processor is configured to perform a first pre-weighting of the image data recorded in the first operating mode and a second pre-weighting of the image data recorded in the second operating mode, wherein the first pre-weighting is different than the second pre-weighting, wherein the second pre-weighting is based on a shift of the X-ray source relative to the first position by the first translation facility in the second operating mode,
   wherein the first pre-weighting is based on pixel coordinates relative to a point of contact of the isocentric beam, and
   wherein the second pre-weighting is based on pixel coordinates relative to a point of impact of a beam striking the surface of the X-ray detector at a substantially perpendicular angle.

2. The imaging facility as claimed in claim 1, wherein the imaging facility is operable in a tomosynthesis mode in which the X-ray source is activated at different translational positions to generate a plurality of image datasets from which a tomosynthesis image is reconstructable.

3. The imaging facility as claimed in claim 1, wherein the first translation facility is operable to automatically move the X-ray source to a position in which the imaging facility compensates for position errors caused by bending of holders on the imaging facility.

4. The imaging facility as claimed in claim 2, wherein the first translation facility is operable to automatically move the X-ray source to a position in which the imaging facility compensates for position errors caused by bending of holders on the imaging facility.

5. The imaging facility as claimed in claim 1, wherein the rotation facility is configured to rotate the X-ray source and the X-ray detector around the center of rotation while the imaging facility is in the first operating mode and in the second operating mode.

6. The imaging facility as claimed in claim 1, wherein the first pre-weighting is based on a comparison of pixel coordinates to coordinates of a first beam striking the surface of the X-ray detector at a substantially perpendicular angle, and the second pre-weighting is based on a comparison of pixel coordinates to coordinates of a second beam striking the surface of the X-ray detector at a substantially perpendicular angle.

7. The imaging facility as claimed in claim 1, wherein the first pre-weighting and second pre-weighting are based on adjusting a projection matrix that reflects the shift of the X-ray detector, and
   wherein pixel coordinates are compared to coordinates of a point of impact of the isometric beam striking the surface of the X-ray detector and coordinates of a point of impact of a beam striking the surface of the X-ray detector at a substantially perpendicular angle for the first pre-weighting and the second pre-weighting, respectively.

8. The imaging facility as claimed in claim 1, wherein the processor unit is configured to reconstruct the three-dimensional image using tomosynthesis using the pre-weighted image data generated from the first pre-weighting and the second pre-weighting.

9. The imaging facility as claimed in claim 1, wherein the processor unit is configured to reconstruct the three-dimensional image using cone beam computed tomograph (CT) using the pre-weighted image data generated from the first pre-weighting and the second pre-weighting.

10. A radiation therapy device comprising:
    a therapeutic radiation source configured to direct a therapeutic treatment beam onto an object to be irradiated; and
    an imaging facility comprising:
    an X-ray source operable to emit a cone beam;

an X-ray detector, wherein the X-ray source, the X-ray detector, or the X-ray source and the X-ray detector are positionable such that an isocentric beam emitted by the X-ray source strikes a surface of the X-ray detector at different angles relative to the surface;

a rotation facility operable to rotate the X-ray source and the X-ray detector around a center of rotation;

a first translation facility configured to move the X-ray source from a first position relative to a portion of the rotation facility, in a direction that has a component that is tangential to a circle of rotation around the center of rotation;

a second translation facility configured to move the X-ray detector from a second position relative to the portion of the rotation facility, wherein the imaging facility is operable in a first operating mode and a second operating mode, wherein in the first operating mode, image data is recorded while the X-ray source and the X-ray detector are aligned with each other such that a central beam of the X-ray source essentially passes through the center of rotation, and wherein in the second operating mode, image data is recorded when the X-ray source and the X-ray detector are moved by the first and second translation facilities to be aligned with each other such that the central beam emitted by the X-ray source runs laterally past the center of rotation; and a processor unit configured to reconstruct a three-dimensional image from the image data recorded while the X-ray source and the X-ray detector are rotated, wherein the processor is configured to perform a first pre-weighting of the image data recorded in the first operating mode and a second pre-weighting of the image data recorded in the second operating mode, wherein the first pre-weighting is different than the second pre-weighting, wherein the second pre-weighting is based on a shift of the X-ray source relative to the first position by the first translation facility in the second operating mode, wherein the first pre-weighting is based on the X-ray source being centered with respect to the X-ray detector, and wherein the second pre-weighting is based on comparison of pixel coordinates to coordinates of a point of impact of a beam striking the surface of the X-ray detector at a substantially perpendicular angle.

11. The radiation therapy device as claimed in claim 10, wherein the imaging facility is arranged in the radiation therapy device to allow the first translation facility to move the X-ray source between at least two imaging positions, and wherein in one of the at least two imaging positions the X-ray source is opposite the therapeutic radiation source.

12. The radiation therapy device as claimed in claim 11, further comprising a holder for the X-ray source, wherein the first translation facility is operable to move the X-ray source from a parked position into an imaging position.

13. The radiation therapy device as claimed in claim 10, further comprising a holder for the X-ray source, wherein the first translation facility is operable to move the X-ray source from a parked position into an imaging position.

14. The imaging facility as claimed in claim 10, wherein the first pre-weighting is based on a comparison of pixel coordinates to coordinates of a first beam striking the surface of the X-ray detector at a substantially perpendicular angle, and the second pre-weighting is based on a comparison of pixel coordinates to coordinates of a second beam striking the surface of the X-ray detector at a substantially perpendicular angle.

15. The imaging facility as claimed in claim 10, wherein the first pre-weighting and the second pre-weighting are based on adjusting a projection matrix that reflects the shift of the X-ray detector, and wherein pixel coordinates are compared to coordinates of a point of impact of the isometric beam striking the surface of the X-ray detector and coordinates of a point of impact of a beam striking the surface of the X-ray detector at a substantially perpendicular angle for the first pre-weighting and the second pre-weighting, respectively.

16. An imaging facility comprising:
an X-ray source operable to emit a cone beam;
an X-ray detector, wherein the X-ray source, the X-ray detector, or the X-ray source and the X-ray detector are positionable such that an isocentric beam emitted by the X-ray source strikes a surface of the X-ray detector at different angles relative to the surface;
a rotation facility operable to rotate the X-ray source and the X-ray detector around a center of rotation;
a first translation facility operable to move the X-ray source in a direction that has a component that is tangential to a circle of rotation around the center of rotation, wherein the imaging facility is operable in a first operating mode and a second operating mode, wherein in the first operating mode, the X-ray detector is configured to record image data while the X-ray source and the X-ray detector are rotated around the center of rotation, and the X-ray source and the X-ray detector are aligned with each other such that a central beam of the X-ray source essentially passes through the center of rotation, and wherein in the second operating mode, the X-ray detector is configured to record image data while the X-ray source and the X-ray detector are rotated around the center of rotation and the X-ray source is moved by the first translation facility such that the central beam emitted by the X-ray source runs laterally past the center of rotation; and
a processor unit configured to reconstruct a three-dimensional image from the image data recorded while the X-ray source and the X-ray detector are rotated and further configured to perform, during the reconstruction, a first weighting of the image data recorded in the first operating mode and a second weighting of the image data recorded in the second operating mode, wherein the first weighting is different than the second weighting, wherein the second weighting is based on a shift of the X-ray source relative to the first position by the first translation facility in the second operating mode,
wherein the first weighting is based on the X-ray source being centered with respect to the X-ray detector, and
wherein the second weighting is based on comparison of pixel coordinates to coordinates of a point of impact of a beam striking the surface of the X-ray detector at a substantially perpendicular angle.

17. The imaging facility as claimed in claim 16, wherein the first weighting is based on a comparison of pixel coordinates to coordinates of a first beam striking the surface of the X-ray detector at a substantially perpendicular angle, and the second weighting is based on a comparison of pixel coordinates to coordinates of a second beam striking the surface of the X-ray detector at a substantially perpendicular angle.

18. The imaging facility as claimed in claim 16, wherein the first weighting is based a first projection matrix that reflects the X-ray source being centered with respect to the X-ray detector, and
wherein the second weighting is based on a second projection matrix that reflects the X-ray source being shifted with respect to the X-ray detector.

19. An imaging facility comprising:
an X-ray source operable to emit a cone beam;
an X-ray detector, wherein the X-ray source, the X-ray detector, or the X-ray source and the X-ray detector are positionable such that an isocentric beam emitted by the X-ray source strikes a surface of the X-ray detector at different angles relative to the surface;
a rotation facility operable to rotate the X-ray source and the X-ray detector around a center of rotation;
a first translation facility configured to move the X-ray source from a first position relative to a portion of the rotation facility in a direction that has a component that is tangential to a circle of rotation around the center of rotation;
a second translation facility configured to move the X-ray detector from a second position relative to the portion of the rotation facility, wherein the imaging facility is operable in a first operating mode and a second operating mode, wherein in the first operating mode, image data is recorded while the X-ray source and the X-ray detector are aligned with each other such that a central beam of the X-ray source essentially passes through the center of rotation, and wherein in the second operating mode, image data is recorded when the X-ray source and the X-ray detector are moved by the first translation facility and the second translation facility, respectively, to be aligned with each other such that the central beam emitted by the X-ray source runs laterally past the center of rotation; and
a processor unit configured to reconstruct a three-dimensional image from the image data recorded while the X-ray source and the X-ray detector are rotated, wherein the processor is configured to perform a first pre-weighting of the image data recorded in the first operating mode and a second pre-weighting of the image data recorded in the second operating mode, wherein the first pre-weighting is different than the second pre-weighting, wherein the second pre-weighting is based on a shift of the X-ray source relative to the first position by the first translation facility in the second operating mode,
wherein the first pre-weighting is based on a comparison of pixel coordinates to coordinates of a first beam striking the surface of the X-ray detector at a substantially perpendicular angle, and the second pre-weighting is based on a comparison of pixel coordinates to coordinates of a second beam striking the surface of the X-ray detector at a substantially perpendicular angle.

20. A radiation therapy device comprising:
a therapeutic radiation source configured to direct a therapeutic treatment beam onto an object to be irradiated; and
an imaging facility comprising:
an X-ray source operable to emit a cone beam;
an X-ray detector, wherein the X-ray source, the X-ray detector, or the X-ray source and the X-ray detector are positionable such that an isocentric beam emitted by the X-ray source strikes a surface of the X-ray detector at different angles relative to the surface;
a rotation facility operable to rotate the X-ray source and the X-ray detector around a center of rotation;
a first translation facility configured to move the X-ray source from a first position relative to a portion of the rotation facility, in a direction that has a component that is tangential to a circle of rotation around the center of rotation;
a second translation facility configured to move the X-ray detector from a second position relative to the portion of the rotation facility, wherein the imaging facility is operable in a first operating mode and a second operating mode, wherein in the first operating mode, image data is recorded while the X-ray source and the X-ray detector are aligned with each other such that a central beam of the X-ray source essentially passes through the center of rotation, and wherein in the second operating mode, image data is recorded when the X-ray source and the X-ray detector are moved by the first and second translation facilities to be aligned with each other such that the central beam emitted by the X-ray source runs laterally past the center of rotation; and
a processor unit configured to reconstruct a three-dimensional image from the image data recorded while the X-ray source and the X-ray detector are rotated, wherein the processor is configured to perform a first pre-weighting of the image data recorded in the first operating mode and a second pre-weighting of the image data recorded in the second operating mode, wherein the first pre-weighting is different than the second pre-weighting, wherein the second pre-weighting is based on a shift of the X-ray source relative to the first position by the first translation facility in the second operating mode,
wherein the first pre-weighting is based on a comparison of pixel coordinates to coordinates of a first beam striking the surface of the X-ray detector at a substantially perpendicular angle, and the second pre-weighting is based on a comparison of pixel coordinates to coordinates of a second beam striking the surface of the X-ray detector at a substantially perpendicular angle.

21. An imaging facility comprising:
an X-ray source operable to emit a cone beam;
an X-ray detector, wherein the X-ray source, the X-ray detector, or the X-ray source and the X-ray detector are positionable such that an isocentric beam emitted by the X-ray source strikes a surface of the X-ray detector at different angles relative to the surface;
a rotation facility operable to rotate the X-ray source and the X-ray detector around a center of rotation;
a first translation facility operable to move the X-ray source in a direction that has a component that is tangential to a circle of rotation around the center of rotation, wherein the imaging facility is operable in a first operating mode and a second operating mode, wherein in the first operating mode, the X-ray detector is configured to record image data while the X-ray source and the X-ray detector are rotated around the center of rotation, and the X-ray source and the X-ray detector are aligned with each other such that a central beam of the X-ray source essentially passes through the center of rotation, and wherein in the second operating mode, the X-ray detector is configured to record image data while the X-ray source and the X-ray detector are rotated around the center of rotation and the X-ray source is moved by the first translation facility such that the central beam emitted by the X-ray source runs laterally past the center of rotation; and
a processor unit configured to reconstruct a three-dimensional image from the image data recorded while the X-ray source and the X-ray detector are rotated and further configured to perform, during the reconstruction, a first weighting of the image data recorded in the first operating mode and a second weighting of the image data recorded in the second operating mode, wherein the first weighting is different than the second weighting, wherein the second weighting is based on a shift of the X-ray source relative to the first position by the first translation facility in the second operating mode, wherein the first weighting is based on a comparison of pixel coordinates to coordinates of a first beam striking the surface of the X-ray detector at a substantially perpendicular angle, and the second weighting is based on a comparison of pixel coordinates to coordinates of a second beam striking the surface of the X-ray detector at a substantially perpendicular angle.

22. An imaging facility comprising:

an X-ray source operable to emit a cone beam;

an X-ray detector, wherein the X-ray source, the X-ray detector, or the X-ray source and the X-ray detector are positionable such that an isocentric beam emitted by the X-ray source strikes a surface of the X-ray detector at different angles relative to the surface;

a rotation facility operable to rotate the X-ray source and the X-ray detector around a center of rotation;

a first translation facility operable to move the X-ray source in a direction that has a component that is tangential to a circle of rotation around the center of rotation, wherein the imaging facility is operable in a first operating mode and a second operating mode, wherein in the first operating mode, the X-ray detector is configured to record image data while the X-ray source and the X-ray detector are rotated around the center of rotation, and the X-ray source and the X-ray detector are aligned with each other such that a central beam of the X-ray source essentially passes through the center of rotation, and wherein in the second operating mode, the X-ray detector is configured to record image data while the X-ray source and the X-ray detector are rotated around the center of rotation and the X-ray source is moved by the first translation facility such that the central beam emitted by the X-ray source runs laterally past the center of rotation; and a processor unit configured to reconstruct a three-dimensional image from the image data recorded while the X-ray source and the X-ray detector are rotated and further configured to perform, during the reconstruction, a first weighting of the image data recorded in the first operating mode and a second weighting of the image data recorded in the second operating mode, wherein the first weighting is different than the second weighting, wherein the second weighting is based on a shift of the X-ray source relative to the first position by the first translation facility in the second operating mode, wherein the first weighting is based a first projection matrix that reflects the X-ray source being centered with respect to the X-ray detector, and wherein the second weighting is based on a second projection matrix that reflects the X-ray source being shifted with respect to the X-ray detector.

* * * * *